(12) United States Patent
Komatsu et al.

(10) Patent No.: US 7,132,292 B2
(45) Date of Patent: Nov. 7, 2006

(54) ANTHER-SPECIFIC PROMOTER FROM THE RICE TUB8 GENE AND USES THEREOF

(75) Inventors: Setsuko Komatsu, Ibaraki (JP); Manabu Yoshikawa, Ibaraki (JP); Guangxiao Yang, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 10/841,604

(22) Filed: May 10, 2004

(65) Prior Publication Data

US 2005/0009061 A1    Jan. 13, 2005

(30) Foreign Application Priority Data

May 12, 2003    (JP)    ............................. 2003-133691

(51) Int. Cl.
- *C07H 21/04* (2006.01)
- *A01H 5/00* (2006.01)
- *C12N 15/82* (2006.01)
- *C12N 5/14* (2006.01)

(52) U.S. Cl. .................. 435/468; 435/320.1; 435/419; 536/24.1

(58) Field of Classification Search ............... 536/24.1; 800/287; 435/320.1

See application file for complete search history.

(56) References Cited

OTHER PUBLICATIONS

Kim et al. (1994) A 20 Nucleotide Upstream Element is Essential for the Nopaline Synthase (nos) Promoter Activity. PMB vol. 24, pp. 105-117.*
Buell R. (2003) GenBank Accession #AC139174.*
Yashikawa et al. (2003) Expression Analyses of B-tubulin Isotype Genes in Rice. Plant Cell Physiol. vol. 44, pp. 1202-1207.*
Jeon et al. (1999) Isolation and Characterization of an Anther-Specific Gene, RA8, from Rice (Oryza sativa L.). PMB vol. 39, pp. 35-44.*
Yoshikawa, M., et al., "Expression Analyses of β-tubulin Isotype Genes in Rice," *Plant Cell Physiol.* 44:1202-1207, Oxford University Press (Nov. 2003).

* cited by examiner

*Primary Examiner*—Ashwin D. Mehta
*Assistant Examiner*—Cathy Kingdon Worley
(74) *Attorney, Agent, or Firm*—Sterne, Kessler, Goldstein & Fox P.L.L.C.

(57) ABSTRACT

The present invention provides novel anther-specific genes, their promoters, and uses of the same. Rice seedlings were treated with gibberellin, and then genes and proteins with up-regulated expression were screened using DNA microarray analysis and proteome analysis. As a result, eight types of β-tubulins were identified. Among them, OsTUB8 was expressed specifically in the anther. Thus OsTUB8 was suggested to be involved in male sterility in rice, and it was thought that regulating OsTUB8 expression in plants could alter plant fertility. In addition, OsTUB8 promoters were thought to comprise anther-specific activity. Thus, the present invention can be said to be highly valuable when used as a tool for anther-specific gene expression.

8 Claims, 4 Drawing Sheets

FIG. 1A

| OsTUB1 | WYT GEGMDEMEFTEAESNMNDLV SEYQQYQDATA DEEGDYEDEEEQVPEDE |
| OsTUB2 | WYT GEGMDEMEFTEAESNMNDLV SEYQQYQDATA DDEGEYEDEEEEADLQD |
| OsTUB3 | WYT GEGMDEMEFTEAESNMNDLV AEYQQYQDATA EEEDYEEEEEDEEVAA |
| OsTUB4 | WYT GEGMDEMEFTEAESNMNDLV SEYQQYQDATA DEEGEYEDEEQQEADDM |
| OsTUB5 | WYT GEGMDEMEFTEAESNMNDLV AEYQQYQDATA DDEEDYGDEEEDEVAA |
| OsTUB6 | WYT GEGMDEMEFTEAESNMNDLV SEYQQYQDATA DEAEYEEEEDAIQE |
| OsTUB7 | WYT GEGMDEMEFTEAESNMNDLV AEYQQYQDATA DEEYEDEEEEAEAE |
| OsTUB8 | WYT SEGMDEMEFTEAESNMNDLV AEYQQYQDATA EDDYDEDDDAAAADEA |

SEQUENCE LISTING

<160> NUMBER OF SEQ ID NOS: 11

<210> SEQ ID NO 1
<211> LENGTH: 1573
<212> TYPE: DNA
<213> ORGANISM: Oryza sativa
<220> FEATURE:
<221> NAME/KEY: CDS
<222> LOCATION: (121)..(1461)
<223> OTHER INFORMATION:

<400> SEQUENCE: 1

```
acgttctcca ccctctctcc atcgatcgat cgcaaaccac ctcccaagaa caaccaagaa      60
agagatcgga tcaccgatcg gcgcgcggcg agcgatcgat cgaggtgcaa gcgatcgaag     120 atg agg gag atc ctg cac atc cag ggc ggg cag tgc ggc aac cag atc      168
Met Arg Glu Ile Leu His Ile Gln Gly Gly Gln Cys Gly Asn Gln Ile
1               5                   10                  15 ggc gcc aag ttc tgg gag gtg atc tgc ggc gag cac ggc gtc gac ccc      216
Gly Ala Lys Phe Trp Glu Val Ile Cys Gly Glu His Gly Val Asp Pro
            20                  25                  30 acg ggg acg tac acc ggc acg tcg ccg cag cag ctc gag cgg atc aac      264
Thr Gly Thr Tyr Thr Gly Thr Ser Pro Gln Gln Leu Glu Arg Ile Asn
        35                  40                  45 gtc tac ttc aac gag gcg agc ggc ggc cgc cac gtc ccg cgc gcc gtg      312
Val Tyr Phe Asn Glu Ala Ser Gly Gly Arg His Val Pro Arg Ala Val
    50                  55                  60 ctc atg gac ctc gag ccg ggc acc atg gac tcg ctc cgc tcc ggc ccc      360
Leu Met Asp Leu Glu Pro Gly Thr Met Asp Ser Leu Arg Ser Gly Pro
65                  70                  75                  80 atc ggc ggc atc ttc cgc ccc gac aac ttc gtc ttc ggc cag tcc ggc      408
Ile Gly Gly Ile Phe Arg Pro Asp Asn Phe Val Phe Gly Gln Ser Gly
                85                  90                  95 gcc ggc aac aac tgg gcc aag ggc cac tac acc gag ggc gcc gag ctc      456
Ala Gly Asn Asn Trp Ala Lys Gly His Tyr Thr Glu Gly Ala Glu Leu
            100                 105                 110 atc gac tcc gtc ctc gac gtc gtc cgc aag gag gcc gag aac tgc gac      504
Ile Asp Ser Val Leu Asp Val Val Arg Lys Glu Ala Glu Asn Cys Asp
        115                 120                 125 tgc ctc caa gga ttc cag gtg tgc cac tcg ctg gga gga ggc acg ggg      552
Cys Leu Gln Gly Phe Gln Val Cys His Ser Leu Gly Gly Gly Thr Gly
    130                 135                 140 tcg ggc atg ggc acg ctg ctc atc tcc aag atc agg gag gag tac ccg      600
Ser Gly Met Gly Thr Leu Leu Ile Ser Lys Ile Arg Glu Glu Tyr Pro
145                 150                 155                 160 gac cgc atg atg ctg acc ttc tcc gtg ttc ccg tcg ccc aag gtg tcg      648
Asp Arg Met Met Leu Thr Phe Ser Val Phe Pro Ser Pro Lys Val Ser
                165                 170                 175 gac acc gtg gtg gag ccc tac aac gcg acg ctg tcc gtg cac cag ctc      696
Asp Thr Val Val Glu Pro Tyr Asn Ala Thr Leu Ser Val His Gln Leu
            180                 185                 190 gtc gag aac gcc gac gag tgc atg gtc ctc gac aac gag gcc ctc tac      744
Val Glu Asn Ala Asp Glu Cys Met Val Leu Asp Asn Glu Ala Leu Tyr
        195                 200                 205 gac atc tgc ttc cgc acc ctc aag ctc acc aac cca tca ttt ggt gac      792
Asp Ile Cys Phe Arg Thr Leu Lys Leu Thr Asn Pro Ser Phe Gly Asp
    210                 215                 220 ctg aac cac ctg ata tcg gcg acg atg agc ggg gtg acg tgc tgc ctg      840
Leu Asn His Leu Ile Ser Ala Thr Met Ser Gly Val Thr Cys Cys Leu
225                 230                 235                 240
```

```
cgg ttc ccg ggg cag ctg aac tcg gac ctg agg aag ctg gcg gtg aac       888
Arg Phe Pro Gly Gln Leu Asn Ser Asp Leu Arg Lys Leu Ala Val Asn
            245                 250                 255 ctg atc ccg ttc ccg cgg ctg cac ttc ttc atg gtg ggg ttc gcg ccg       936
Leu Ile Pro Phe Pro Arg Leu His Phe Phe Met Val Gly Phe Ala Pro
        260                 265                 270 ctg acg tcg cgc ggg tcg cag cag tac agg gcg ctg acg gtg ccg gag       984
Leu Thr Ser Arg Gly Ser Gln Gln Tyr Arg Ala Leu Thr Val Pro Glu
    275                 280                 285 ctg acg cag cag atg tgg gac gcc aag aac atg atg tgc gcc gcc gac      1032
Leu Thr Gln Gln Met Trp Asp Ala Lys Asn Met Met Cys Ala Ala Asp
290                 295                 300 ccg cgc cac ggc cgc tac ctc acg gcg tcc gcc atg ttc cgg ggc agg      1080
Pro Arg His Gly Arg Tyr Leu Thr Ala Ser Ala Met Phe Arg Gly Arg
305                 310                 315                 320 atg agc acc aag gag gtg gac gag cag atg atc aac gtg cag aac aag      1128
Met Ser Thr Lys Glu Val Asp Glu Gln Met Ile Asn Val Gln Asn Lys
            325                 330                 335 aac tcg tcc tac ttc gtg gag tgg atc ccc aac aac gtc aag tcc agc      1176
Asn Ser Ser Tyr Phe Val Glu Trp Ile Pro Asn Asn Val Lys Ser Ser
        340                 345                 350 gtc tgc gac atc ccc ccc gtc ggc ctc tcc atg gcg tcc acc ttc gtc      1224
Val Cys Asp Ile Pro Pro Val Gly Leu Ser Met Ala Ser Thr Phe Val
    355                 360                 365 ggc aac tcc acc tcc atc cag gag atg ttc cgc cgc gtc agc gag cag      1272
Gly Asn Ser Thr Ser Ile Gln Glu Met Phe Arg Arg Val Ser Glu Gln
370                 375                 380 ttc acc gcc atg ttc cgc cgc aag gcc ttc ctc cac tgg tac acc agc      1320
Phe Thr Ala Met Phe Arg Arg Lys Ala Phe Leu His Trp Tyr Thr Ser
385                 390                 395                 400 gag gga atg gac gag atg gag ttc acc gag gcc gag agc aac atg aac      1368
Glu Gly Met Asp Glu Met Glu Phe Thr Glu Ala Glu Ser Asn Met Asn
            405                 410                 415 gac ctc gtc gcc gag tac cag cag tac cag gac gcc acc gcc gag gac      1416
Asp Leu Val Ala Glu Tyr Gln Gln Tyr Gln Asp Ala Thr Ala Glu Asp
        420                 425                 430 gac tac gac gag gac gac gac gcc gcc gcc gcc gac gag gcc tga          1461
Asp Tyr Asp Glu Asp Asp Asp Ala Ala Ala Ala Asp Glu Ala
    435                 440                 445 tcgatcgatc gatcgatccc tcccgctttg cctctctggc tctctgctac gctacgctac    1521
atatatttcg atcggtacaa acacacaatg tgccgttgcs cgtgtctgct gc            1573
```

<210> SEQ ID NO 2
<211> LENGTH: 446
<212> TYPE: PRT
<213> ORGANISM: Oryza sativa

<400> SEQUENCE: 2

```
Met Arg Glu Ile Leu His Ile Gln Gly Gly Gln Cys Gly Asn Gln Ile
1               5                   10                  15

Gly Ala Lys Phe Trp Glu Val Ile Cys Gly Glu His Gly Val Asp Pro
            20                  25                  30

Thr Gly Thr Tyr Thr Gly Thr Ser Pro Gln Gln Leu Glu Arg Ile Asn
        35                  40                  45

Val Tyr Phe Asn Glu Ala Ser Gly Gly Arg His Val Pro Arg Ala Val
    50                  55                  60

Leu Met Asp Leu Glu Pro Gly Thr Met Asp Ser Leu Arg Ser Gly Pro
65                  70                  75                  80
```

-continued

```
Ile Gly Gly Ile Phe Arg Pro Asp Asn Phe Val Phe Gln Ser Gly
                 85                  90                  95

Ala Gly Asn Asn Trp Ala Lys Gly His Tyr Thr Glu Gly Ala Glu Leu
            100                 105                 110

Ile Asp Ser Val Leu Asp Val Arg Lys Glu Ala Glu Asn Cys Asp
            115                 120                 125

Cys Leu Gln Gly Phe Gln Val Cys His Ser Leu Gly Gly Thr Gly
    130                 135                 140

Ser Gly Met Gly Thr Leu Leu Ile Ser Lys Ile Arg Glu Glu Tyr Pro
145                 150                 155                 160

Asp Arg Met Met Leu Thr Phe Ser Val Phe Pro Ser Pro Lys Val Ser
                165                 170                 175

Asp Thr Val Val Glu Pro Tyr Asn Ala Thr Leu Ser Val His Gln Leu
                180                 185                 190

Val Glu Asn Ala Asp Glu Cys Met Val Leu Asp Asn Glu Ala Leu Tyr
            195                 200                 205

Asp Ile Cys Phe Arg Thr Leu Lys Leu Thr Asn Pro Ser Phe Gly Asp
    210                 215                 220

Leu Asn His Leu Ile Ser Ala Thr Met Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Ile Pro Phe Pro Arg Leu His Phe Phe Met Val Gly Phe Ala Pro
            260                 265                 270

Leu Thr Ser Arg Gly Ser Gln Gln Tyr Arg Ala Leu Thr Val Pro Glu
    275                 280                 285

Leu Thr Gln Gln Met Trp Asp Ala Lys Asn Met Met Cys Ala Ala Asp
    290                 295                 300

Pro Arg His Gly Arg Tyr Leu Thr Ala Ser Ala Met Phe Arg Gly Arg
305                 310                 315                 320

Met Ser Thr Lys Glu Val Asp Glu Gln Met Ile Asn Val Gln Asn Lys
                325                 330                 335

Asn Ser Ser Tyr Phe Val Glu Trp Ile Pro Asn Asn Val Lys Ser Ser
            340                 345                 350

Val Cys Asp Ile Pro Pro Val Gly Leu Ser Met Ala Ser Thr Phe Val
    355                 360                 365

Gly Asn Ser Thr Ser Ile Gln Glu Met Phe Arg Arg Val Ser Glu Gln
    370                 375                 380

Phe Thr Ala Met Phe Arg Arg Lys Ala Phe Leu His Trp Tyr Thr Ser
385                 390                 395                 400

Glu Gly Met Asp Glu Met Glu Phe Thr Glu Ala Glu Ser Asn Met Asn
                405                 410                 415

Asp Leu Val Ala Glu Tyr Gln Gln Tyr Gln Asp Ala Thr Ala Glu Asp
            420                 425                 430

Asp Tyr Asp Glu Asp Asp Ala Ala Ala Asp Glu Ala
    435                 440                 445

<210> SEQ ID NO 3
<211> LENGTH: 1942
<212> TYPE: DNA
<213> ORGANISM: Oryza sativa
```

-continued

```
<400> SEQUENCE: 3
atatatgtat gtacaatgac ttgatgatca tcatgataat gatgcgaaag aaatcaagaa     60
cagcatcttc tccttgcaaa tgccatggca acagtatttg aacgtgacaa aggctagagc    120
aatgtaacac tatggacaag ttgacagcta acttttctct tgatatctat ttatattaat    180
cataaaaaga acacttgttg gccaagctgt ctccgtactt tttcgagcac acaataagtc    240
ataccaaact tggtttaaat atactaataa caatcagtgt acttgttttc tcattttctc    300
ttcattggca ggggagtgta ctttcttagg gtattcttcc gttccaaaat caatcgactt    360
gtccagattt acatacaaaa gattattaaa ttttaaaaaa tataaattat tttaaaagaa    420
agggagtagt aaattgtgca tatgtatgta tattatatat atatatatat atatatatat    480
atattcacgt acgaaagaaa ttcattttaa aaggttcttc ttcctctaaa atagtattac    540
ctccgtttta gattataaaa ctttctacga ttgtctatat ttatatatat gttaatgaat    600
cttgacacat ataagtacca gtactatgta ctctcacatg tgaactactc cctctatccc    660
aaaaaaagcc aacttctggc tatgtgcaag tagagaacta gtgaactact tcctctgtta    720
agaaaataaa cctactacaa aacgtgacac attatagtgt tgtaaatttg tataggagga    780
ctgcttaaat ttgtagaact aggatgtgtt atatttagga cgaaggaagt agtacatatc    840
aaaattccca aggatgtac acatgtggac gtgtaaatga agagatttta tgacagtctc    900
taccaggtaa caaaggcctt taaaattaat atggatccat tcctcttgag acacgcctta    960
aaaaattttg acattcagaa atactactag tggcaaatat gccaatataa tgtgccctct   1020
aataacatat aactatcttt caaaaaaagt tgtaccaaaa aaaaaactta ccccatacta   1080
atactgtagt agaaaagtag tgctccatga ttttgctatt ttcttcctct gatctgtaac   1140
taggcctaag tgtgcttgca ggtaccaaat tgatccgtag taaattagca ttgatcccat   1200
tatttggtga cccgccactg cacccagcca aaaataaaat gtggcagaaa aaatagacag   1260
cacaacgtga tcgtccccac accccttga taccacagta cctcatgcgg tctaccctgg   1320
cacatcttta catactcatg gagtcatggt ctacacaggt acttcaatac tcacatccat   1380
aattccatat cgctaattaa acgaacatt tagtacaact agatttatac ctgacctgca   1440
acaaatccac aacaaaattt ttagtattct ctccgtttta tattataagt catttcaact   1500
ttatatttaa tcaagtttat agaaaaaaat aacatcttta acatcatatt agtgtaacat   1560
tcagtatatc ttgacaatat gtttgtttat gttaaaaata ctattgcatt tatattagga   1620
aaaaaattaa aacgatttat aatataaaac agatgtccac acaaattaag tacttcgctt   1680
gatcaacctt tcttttgcaa taaccaaaac acactcagac caaaaataac gcgtcaccta   1740
taaaatttta agttccaaa gaaaccgtc tctttaaaat tcgaagacaa ccgtaaaaaa   1800
ataaataaat tgaagcgata tcaatacgtg taagcatttg tccatacacc tggtccacgc   1860
acaaccataa cacccagaaa gagaagcggt tccctccaaa cgcgggatat aagcgcccac   1920
gatccctcct cctctccttc cc                                             1942

<210> SEQ ID NO 4
<211> LENGTH: 51
<212> TYPE: PRT
<213> ORGANISM: Oryza sativa
```

```
<400> SEQUENCE: 4

Trp Tyr Thr Gly Glu Gly Met Asp Glu Met Glu Phe Thr Glu Ala Glu
1               5                   10                  15

Ser Asn Met Asn Asp Leu Val Ser Glu Tyr Gln Gln Tyr Gln Asp Ala
            20                  25                  30

Thr Ala Asp Glu Glu Gly Asp Tyr Glu Asp Glu Glu Gln Val Pro
        35                  40                  45

Glu Asp Glu
    50

<210> SEQ ID NO 5
<211> LENGTH: 51
<212> TYPE: PRT
<213> ORGANISM: Oryza sativa

<400> SEQUENCE: 5

Trp Tyr Thr Gly Glu Gly Met Asp Glu Met Glu Phe Thr Glu Ala Glu
1               5                   10                  15

Ser Asn Met Asn Asp Leu Val Ser Glu Tyr Gln Gln Tyr Gln Asp Ala
            20                  25                  30

Thr Ala Asp Asp Glu Gly Glu Tyr Glu Asp Glu Glu Glu Ala Asp
        35                  40                  45

Leu Gln Asp
    50

<210> SEQ ID NO 6
<211> LENGTH: 50
<212> TYPE: PRT
<213> ORGANISM: Oryza sativa

<400> SEQUENCE: 6

Trp Tyr Thr Gly Glu Gly Met Asp Glu Met Glu Phe Thr Glu Ala Glu
1               5                   10                  15

Ser Asn Met Asn Asp Leu Val Ala Glu Tyr Gln Gln Tyr Gln Asp Ala
            20                  25                  30

Thr Ala Glu Glu Glu Asp Tyr Glu Glu Glu Glu Asp Glu Glu Val
        35                  40                  45

Ala Ala
    50

<210> SEQ ID NO 7
<211> LENGTH: 51
<212> TYPE: PRT
<213> ORGANISM: Oryza sativa

<400> SEQUENCE: 7

Trp Tyr Thr Gly Glu Gly Met Asp Glu Met Glu Phe Thr Glu Ala Glu
1               5                   10                  15

Ser Asn Met Asn Asp Leu Val Ser Glu Tyr Gln Gln Tyr Gln Asp Ala
            20                  25                  30

Thr Ala Asp Glu Glu Gly Glu Tyr Glu Asp Glu Glu Gln Glu Ala
        35                  40                  45

Asp Asp Met
    50
```

```
<210> SEQ ID NO 8
<211> LENGTH: 51
<212> TYPE: PRT
<213> ORGANISM: Oryza sativa

<400> SEQUENCE: 8

Trp Tyr Thr Gly Glu Gly Met Asp Glu Met Glu Phe Thr Glu Ala Glu
1               5                   10                  15

Ser Asn Met Asn Asp Leu Val Ala Glu Tyr Gln Gln Tyr Gln Asp Ala
            20                  25                  30

Thr Ala Asp Asp Glu Glu Glu Asp Tyr Gly Asp Glu Glu Glu Asp Glu
        35                  40                  45

Val Ala Ala
    50

<210> SEQ ID NO 9
<211> LENGTH: 48
<212> TYPE: PRT
<213> ORGANISM: Oryza sativa

<400> SEQUENCE: 9

Trp Tyr Thr Gly Glu Gly Met Asp Glu Met Glu Phe Thr Glu Ala Glu
1               5                   10                  15

Ser Asn Met Asn Asp Leu Val Ser Glu Tyr Gln Gln Tyr Gln Asp Ala
            20                  25                  30

Thr Ala Asp Glu Ala Glu Tyr Glu Glu Glu Asp Ala Ile Gln Glu
        35                  40                  45

<210> SEQ ID NO 10
<211> LENGTH: 48
<212> TYPE: PRT
<213> ORGANISM: Oryza sativa

<400> SEQUENCE: 10

Trp Tyr Thr Gly Glu Gly Met Asp Glu Met Glu Phe Thr Glu Ala Glu
1               5                   10                  15

Ser Asn Met Asn Asp Leu Val Ala Glu Tyr Gln Gln Tyr Gln Asp Ala
            20                  25                  30

Thr Ala Asp Glu Glu Tyr Glu Asp Glu Glu Glu Glu Ala Glu Ala Glu
        35                  40                  45

<210> SEQ ID NO 11
<211> LENGTH: 50
<212> TYPE: PRT
<213> ORGANISM: Oryza sativa

<400> SEQUENCE: 11

Trp Tyr Thr Ser Glu Gly Met Asp Glu Met Glu Phe Thr Glu Ala Glu
1               5                   10                  15

Ser Asn Met Asn Asp Leu Val Ala Glu Tyr Gln Gln Tyr Gln Asp Ala
            20                  25                  30

Thr Ala Glu Asp Asp Tyr Asp Glu Asp Asp Asp Ala Ala Ala Ala Asp
        35                  40                  45

Glu Ala
    50
```

ANTHER-SPECIFIC PROMOTER FROM THE RICE TUB8 GENE AND USES THEREOF

FIELD OF THE INVENTION

The present invention relates to anther-specific genes, their gene promoters, and uses of the same.

BACKGROUND OF THE INVENTION

Male sterile crops are industrially important in that they help avoid negative influences pollen dispersal has on the ecosystem, and facilitate plant crossings for selective breeding. Thus, it is hoped that plant gene recombination technology can solve food and environmental problems that are fast becoming modern-day issues. However, as many Japanese consumers are anxious about negative effects genetically modified crops may have on health and the ecosystem, the commercialization of these food products tends to be suppressed. Male sterility generating technology has important implications in solving these problems. In many crops, large numbers of male sterile strains are currently being selected and preserved as a genetic resource to facilitate crossing with other strains in selective breeding.

For this reason, there have been many attempts to produce male sterile crops. For example, a male sterile rapeseed produced by genetic recombination has already been commercialized. It has been reported that calcium- and calmodulin-dependent protein kinases are specifically expressed in the pollen-forming phase, and that recombinant plants with inhibited expression of these genes do not form pollen with normal germinability, causing male sterile plants (Takezawa, D. et al., U.S. Pat. No. 6,077,991, Jun. 20, 2000). In addition, a region that specifically regulates gene expression in pollen has been detected in the expression regulation region (promoter) of the proton translocating pyrophosphatase gene in the tonoplast membrane of Arabidopsis. Transformants in which gene expression is inhibited using this region are reported to become male sterile (Sato, Kyoto University, 2002).

SUMMARY OF THE INVENTION

The present invention provides novel anther-specific genes, their gene promoters, and uses of the same.

Gibberellin is largely involved in regulating the intrinsic life cycle of rice. Specifically, gibberellin 1) lengthens stems and leaves (elongation/growth stimulatory effect), 2) enlarges fruits without fertilization (parthenocarpy), 3) speeds flowering (flowering acceleration), and 4) germinates dormant seeds (dormancy breaking), etc. There are many reports on current research regarding rice in which enzymes involved in gibberellin biosynthesis have been mutated. However, much remains unclear as to how gibberellin's signals are transmitted, to exhibit different forms. Thus, with the aim of elucidating the molecular mechanism of gibberellin function, rice seedling were treated with gibberellin, and genes and proteins with enhanced expression were investigated using DNA microarrays and proteome analysis.

As a result, β-tubulin genes were identified. Tubulins are major components of the cytoskeleton, and have the α-type and β-type. In eukaryotes, these proteins function in a variety of ways, for example in cell division and elongation, as well as in cell movement, nuclear division, and cytokinesis. In particular, tubulins regulate the orientation of cellulose microfiber deposits. Therefore, the tubulins identified by the present inventors are thought to influence stem and leaf elongation in rice by being involved in cell elongation. In addition, as a result of screening for β-tubulins in rice, eight types of β-tubulins were detected. Of these eight types of tubulins that were identified, OsTUB8 was shown to be specifically expressed in the anther. Thus, OsTUB8 was suggested to be involved with male sterility in rice. It is thought that regulating OsTUB8 expression in plants alters plant fertility.

In addition, since OsTUB8 promoters are thought to comprise anther-specific activity, they are extremely useful as tools for anther-specific gene expression.

Thus, the present invention relates to novel anther-specific genes, their promoters, and the uses of the same. Specifically, the present invention relates to the following:

[1] an isolated DNA of any one of the following (a) to (d);
(a) a DNA encoding the amino acid sequence of SEQ ID NO: 2;
(b) a DNA comprising the nucleotide sequence of SEQ ID NO: 1;
(c) a DNA encoding encoding a protein which is (i) functionally equivalent to a protein comprising the amino acid sequence of SEQ ID NO: 2, and (b) comprises the amino acid sequence of SEQ ID NO: 2, wherein one or more amino acids are substituted, deleted, added, and/or inserted; and
(d) a DNA that (i) encodes a protein which is functionally equivalent to the protein comprising the amino acid sequence of SEQ ID NO: 2, and (ii) hybridizes under stringent conditions to the DNA comprising the nucleotide sequence of SEQ ID NO: 1;

[2] a DNA encoding an antisense RNA that is complementary to the transcription product of the DNA of SEQ ID NO: 1;

[3] a DNA encoding an RNA that comprises ribozyme activity that specifically cleaves the transcription product of the DNA of SEQ ID NO: 1;

[4] a DNA encoding an RNA that down-regulates expression of the DNA of SEQ ID NO: 1 by the co-suppression effect when expressed in plant cells;

[5] a DNA encoding a protein that comprises a characteristic that is dominant-negative for an endogenous protein in plant cells encoded by the DNA of [1];

[6] a vector comprising a DNA of any one of [1] to [5];

[7] a transformed plant cell to which a DNA of any one of [1] to [5] or the vector of [6] is introduced;

[8] a transformed plant comprising the transformed plant cell of [7];

[9] a transformed plant clone or offspring of the transformed plant of [8];

[10] a reproductive material from the transformed plant of [8] or [9];

[11] a DNA of any one of the following (a) to (c) that comprises anther-specific promoter activity:
(a) a DNA comprising the nucleotide sequence of SEQ ID NO: 3;
(b) a DNA comprising the nucleotide sequence of SEQ ID NO: 3, wherein one or more nucleotides are substituted, deleted, added, and/or inserted; and
(c) a DNA that hybridizes under stringent conditions to the DNA comprising the nucleotide sequence of SEQ ID NO: 3;

[12] a vector comprising the DNA of [11];

[13] the vector of [12] that is operably linked to an arbitrary gene downstream of the DNA of [11];

[14] a transformed plant cell comprising the vector of [13];

[15] a transformed plant comprising the transformed plant cell of [14];

[16] a transformed plant clone or offspring of the transformed plant of [15]; and

[17] a reproductive material from the transformed plant of [15] or [16].

BRIEF DESCRIPTION OF THE DRAWINGS

FIG. 2 shows photographs showing the hormone specificity of β-tubulins. After treatment with each hormone, Northern blotting using specific probes was performed to confirm the mRNA expression in rice leaf sheaths. C: No treatment; GA: gibberellin; BL: brassinolide; ABA: abscisic acid; IAA: auxin; BA: cytokinin. OsTUA2 shows α-tubulin.

FIG. 3 depicts photographs showing β-tubulin specificity in tissues. Using specific probes, Northern blotting was performed to confirm the expression levels of mRNA in each rice tissue. R: roots; LS: leaf sheaths; L: leaves, N: nodes; A: anthers; SC: cultured cells.

DETAILED DESCRIPTION OF THE INVENTION

The present invention provides DNAs encoding OsTUB8 proteins. The nucleotide sequence of the OsTUB8 cDNA in rice, Nipponbare, is set forth in SEQ ID NO: 1, and the amino acid sequence of the protein encoded by the DNA is shown in SEQ ID NO: 2.

The DNAs encoding the OsTUB8 proteins of the present invention include genomic DNAs, cDNAs, and chemically synthesized DNAs. One skilled in the art can prepare genomic DNAs and cDNAs using conventional methods. Genomic DNAs can be prepared, for example, by extracting them from a rice variety (for example, Nipponbare) comprising an OsTUB8 gene, constructing a genomic library (where plasmids, phages, cosmids, BAC, PAC, and such can be used as a vector), developing this library, and then carrying out colony or plaque hybridization using probes prepared based on DNAs (for example, SEQ ID NO: 1) encoding a protein of the present invention. In addition, such DNAs can also be prepared by carrying out PCRs using primers constructed to be specific to a DNA (for example, SEQ ID NO: 1) encoding a protein of the present invention. Equally, cDNAs can be prepared by: for example, 1) extracting mRNAs from a rice variety (for example, Nipponbare) comprising an OsTUB8 gene; 2) constructing cDNAs based on the mRNAs; 3) inserting these cDNAs into a λZAP vector or the like; 4) constructing a cDNA library; 5) developing this library; and then, as outlined above, 6) carrying out colony or plaque hybridization, or PCR.

The present invention includes DNAs that encode proteins functionally equivalent to the OsTUB8 protein (Nipponbare) set forth in SEQ ID NO: 2. Herein, "proteins functionally equivalent to the OsTUB8 protein (Nipponbare)" means target proteins that comprise a biological or biochemical function equivalent to the OsTUB8 protein. An example of such a function is anther-specific expression. Anther-specific expression means expression in the anther, that is at least five times or more, preferably ten times or more, and more preferably 15 times or more than the expression in the non-anther tissues listed in Example 3. For example, as in Example 3, to evaluate whether a test gene encodes a protein specifically expressed in a plant's anther, mRNAs can be extracted from each of the plant's tissues, and Northern blotting analysis can be carried out using oligonucleotide probes that hybridize to the test genes.

Examples of other functions include induction of plant fertility and functions as tubulins (in cell division, cell elongation, cell mobility, nuclear division, cytokinesis, regulation of cellulose fibre deposit orientation). To evaluate whether a test gene comprises these functions, test gene expression in the plant can be suppressed using antisense technology or the like, and the resulting plant phenotype can be analyzed.

DNAs that encode proteins functionally equivalent to the OsTUB8 protein (Nipponbare) described in SEQ ID NO: 2 are preferably derived from monocotyledons, more preferably from Gramineae, and most preferably from rice.

Such DNA include, for example, homologues, variants, alleles, derivatives, and mutants, which encode a protein comprising the amino acid sequence of SEQ ID NO: 2, in which one or more amino acids are substituted, deleted, added, or inserted.

Site-directed mutagenesis is a well known method for preparing DNAs that encode a protein whose amino acid sequence is artificially altered (Kramer, W. and Fritz, H. J., 1987, "Oligonucleotide-directed construction of mutations via gapped duplex DNA.", Methods in Enzymology, 154: 350–367). In addition, mutations in amino acid sequences of proteins can naturally occur due to mutations in the coding nucleotide sequences. So long as a DNA encodes a protein functionally equivalent to a natural OsTUB8 protein (SEQ ID NO: 2), that DNA can be included as a DNA of the present invention, even if the amino acid sequence of the natural-type OsTUB8 protein includes one or more amino acid substitutions, deletions, additions, or insertions. The DNAs of the present invention also include conservative mutants in which nucleotides are mutated without resulting in mutation of the protein amino acid sequence (conservative mutations).

Other methods that can be used to prepare DNAs that encode proteins functionally equivalent to the OsTUB8 protein described in SEQ ID NO: 2 include hybridization technology (Southern, E. M., 1975, Journal of Molecular Biology, 98: 503–517) and polymerase chain reaction (PCR) (Saiki, R. K. et al., 1985, Science, 230: 1350–1354; Saiki, R. K. et al., 1988, Science, 239: 487–491), which are well known to those skilled in the art. Namely, it is routine experimentation for one skilled in the art to isolate DNAs highly homologous to the OsTUB8 gene from rice or other plants by using the nucleotide sequence of the OsTUB8 gene (SEQ ID NO: 1) or a part of it as a probe, and an oligonucleotide that specifically hybridizes to a nucleotide sequence of the OsTUB8 gene (SEQ ID NO: 1) as a primer. DNAs which are isolated in this way, using hybridization, PCR technology, and such, and which encode proteins functionally equivalent to an OsTUB8 protein, are also included in the DNAs of the present invention. To isolate such DNA, hybridization reactions are preferably carried out under stringent conditions. In the present invention, stringent hybridization conditions means 6 M urea, 0.4% SDS, and 0.5×SSC, or stringent hybridization conditions equivalent to these. Under more stringent conditions, for example, 6 M urea, 0.4% SDS, and 0.1×SSC, DNAs with greater homology are expected to be isolated. At the amino acid level, DNAs thus isolated are thought to be highly homologous to the amino acid sequence of the OsTUB8 protein (SEQ ID NO: 2). High homology means sequence identity, over the entire amino acid sequence, of at least 50% or more, preferably 70% or more, and more preferably 90% or more (for example, 95%, 96%, 97%, 98%, and 99% or more).

Amino acid and nucleotide sequence identity can be determined using the BLAST algorithm (Karlin, S. and Altschul, S. F., 1993, Proc. Natl. Acad. Sci. USA, 90: 5873–5877). Based on this algorithm, programs called BLASTN and BLASTX were developed (Altschul, S. F. et al., 1990, J. Mol. Biol. 215: 403–410). When analyzing nucleotide sequences with BLASTN based on BLAST, parameters can be set as, for example, score=100 and wordlength=12. When analyzing amino acid sequences using BLASTX based on BLAST, parameters can be set as, for example, score=50 and wordlength=3. When using the BLAST and Gapped BLAST programs, each program's default parameters are used. The fundamental steps of these analysis methods are publicly available (http://www.ncbi.nlm.nih.gov/).

The above OsTUB8 protein-coding DNAs of the present invention can be used for isolating DNAs comprising anther-specific promoter activity. For example, genomic DNAs upstream of a DNA encoding the OsTUB8 protein of the present invention can be acquired by using a DNA of the present invention, or a part of it, as a probe to screen a genomic DNA library. Since these upstream genomic DNAs are thought to comprise anther-specific promoter activity, they have high industrial value when used to specifically express arbitrary genes in the anther. In addition, since the DNAs that encode the OsTUB8 protein of the present invention are expressed specifically in plant anthers, they are also thought to be useful as markers for tissues that differentiate into anthers during the process of plant development. As a further example, the DNAs that encode the OsTUB8 protein of the present invention are also thought to be useful in granting fertility to male sterile plants. In other words, it is thought fertility can be granted to male sterile plants by inserting a DNA encoding an OsTUB8 protein of the present invention into a suitable vector, introducing this vector into plant cells that comprise the characteristic of male sterility, and then regenerating the resulting recombinant plant cells. Since male sterile varieties cannot self-pollinate, attempting to maintain them is difficult, even when those varieties comprise excellent characteristics. However, if fertility can be recovered using a DNA that encodes an OsTUB8 protein, self-pollination becomes possible, as does the maintenance of excellent qualities. DNAs encoding the OsTUB8 protein are also useful from this perspective.

Recombinant plants with suppressed expression of a DNA encoding an OsTUB8 protein of the present invention can also be produced by: 1) inserting a DNA for suppressing the expression of a DNA encoding an OsTUB8 protein of the present invention into an appropriate vector; 2) introducing this vector into plant cells; and 3) regenerating the recombinant plant cells thus obtained. In the present invention, the phrase "suppressing the expression of a DNA" includes suppressing translation to a protein as well as suppressing DNA transcription. In addition to complete arrest of DNA expression, reduced DNA expression is also included in the phrase.

Antisense technology is the most commonly-used methods by those skilled in the art to suppress the expression of specific endogenous genes in plants. The antisense effect in plant cells was first proved by Ecker, J. R et al. Specifically, they used transient gene expression methods in plants to demonstrate the antisense effect of antisense RNA inserted by electrophoresis (Ecker, J. R. and Davis, R. W, 1986, Proc. Natl. Acad. Sci. USA, 83: 5372–5376). Following this, there were reports of examples where target gene expression in tobacco and petunia plants were also reduced by antisense RNA expression (such as van der Krol, A. R. et al., 1988, Nature, 333: 866–869). Antisense technology is now an established method for suppressing gene expression in plants.

There are a number of important factors involved in the action of antisense nucleic acids in suppressing target gene expression, as indicated as follows: inhibiting transcription initiation by forming triple strands; suppressing transcription by hybridizing with a site where RNA polymerase has formed a local open loop structure; inhibiting transcription by hybridizing with the RNA being synthesized; suppressing splicing by hybridizing with an intron-exon junction; suppressing splicing by hybridizing with the site of spliceosome formation; suppressing transfer from the nucleus to the cytoplasm by hybridizing with mRNA; suppressing splicing by hybridizing with a poly (A) addition site or capping site; suppressing translation initiation by hybridizing with a translation initiation factor binding site; suppressing translation by hybridizing with a ribosome binding site near the initiation codon; preventing peptide chain elongation by hybridizing with a mRNA translation region or polysome binding site; and suppressing gene expression by hybridizing with a nucleic acid-protein interaction site. These antisense nucleic acids suppress target gene expression by inhibiting transcription, splicing, or translation process (Hirashima and Inoue, 1993, "Shin Seikagaku Jikken Kouza (New Biochemistry Experimentation Lectures) 2, Kakusan (Nucleic Acids) IV, Idenshi No Fukusei To Hatsugen (Replication and Expression of Genes)", Nihon Seikagakukai Hen (The Japanese Biochemical Society) Ed., Tokyo Kagaku Dojin, pp. 319–347).

The antisense sequences used in the present invention can inhibit the expression of a target gene by any of the above actions. As one embodiment, an antisense sequence designed to be complementary to an untranslated region close to the 5' end of the mRNA of a gene will be effective in inhibiting translation of that gene. However, a sequence complementary to a coding region, or to a 3'-end untranslated region can also be used. In this way, DNAs comprising antisense sequences of a gene's translated regions as well untranslated regions are included in the antisense DNAs that can be used in the present invention. An antisense DNA to be used herein is ligated downstream of an appropriate promoter (for example, OsTUB8 promoter as described below), and a sequence comprising a transcription termination signal is preferably ligated to the 3' side of the DNA. DNAs thus prepared can be transfected into a desired plant using known methods. Antisense DNA sequences are preferably sequences complementary to an endogenous gene, or a part thereof, of the plant to be transformed, but need not be perfectly complementary as long as they can effectively inhibit gene expression. The transcribed RNA is preferably 90% or more, and more preferably 95% or more (for example, 96%, 97%, 98%, 99%, or more) complementary to the transcribed products of the target gene. In order to effectively inhibit target gene expression using an antisense sequence, an antisense DNA should comprise at least 15 nucleotides or more, preferably 100 nucleotides or more, and even more preferably 500 nucleotides or more. Antisense DNAs to be used are generally less than 5 kb, and preferably less than 2.5 kb long.

Suppression of endogenous gene expression can also be carried out using DNAs encoding ribozymes. Ribozymes refer to RNA molecules that comprise catalytic activity. Ribozymes can comprise many different activities. Among them, research on ribozymes as RNA-cleaving enzymes has revealed that ribozymes can be designed to cleave specific RNA sites. Ribozymes can be larger than 400 nucleotides, such as M1RNA in RnaseP, or the group 1 intron type ribozymes. In contrast, there are also hammerhead-type or hairpin-type ribozymes that comprise an active domain of about 40 nucleotides (Koizumi, M. and Ohtsuka, E., 1990, Tanpakushitsu Kakusan Kohso (Nucleic acid, Protein, and Enzyme), 35: 2191–2200).

For example, the self-cleaving domain of a hammerhead type ribozyme cleaves at the 3' side of C15 in G13U14C15. Base pairing between U14 and A9 is important for ribozyme activity. It has been shown that cleavage can occur if A or U instead of C is at the fifteenth position (Koizumi, M. et al., 1988, FEBS Lett. 228: 228–230). If the substrate-binding site of the ribozyme is designed to be complementary to the RNA sequences adjacent to the target site, a restriction enzyme-like RNA-cleaving ribozyme can be created that recognizes the sequence UC, UU, or UA within the target RNA (Koizumi, M. et al., 1988, FEBS Lett. 239: 285–288; Koizumi, M. and Ohtsuka, E., 1990, Tanpakushitsu Kakusan Kohso (Protein, Nucleic acid, and Enzyme), 35: 2191–2200; Koizumi, M. et al., 1989, Nucleic Acids Res. 17: 7059–7071). For example, there are many sites that can be targeted in the OsTUB8 gene coding region (SEQ ID NO: 1).

Hairpin type ribozymes are also useful for the aims of the present invention. A hairpin type ribozyme can be found, for example, in the minus strand of tobacco ringspot virus satellite RNA (Buzayan, J. M., et al., 1986, Nature 323, 349–353). It has also been shown that this ribozyme can be designed to target-specifically cleave RNA (Kikuchi, Y. and Sasaki, N., 1991, Nucleic Acids Res. 19: 6751–6755; Kikuchi, Y., 1992, Kagaku to Seibutsu (Chemistry and Biology) 30, 112–118).

In order to be transcribed in plant cells, a ribozyme designed to cleave a target can be linked to a transcription termination sequence or a promoter sequence such as the cauliflower mosaic virus 35S promoter. However, if extra sequences are added to the 5' or the 3' end of the transcribed RNA, the ribozyme activity can be lost. In this case, another trimming ribozyme, which functions in the cis position, can be placed in the 5' or 3' side of the ribozyme portion to precisely trim only the ribozyme portion from the transcribed RNA comprising the ribozyme (Taira, K. et al., 1990, Protein Eng. 3: 733–737; Dzianot, A. M. and Bujarski, J. J., 1989, Proc. Natl. Acad. Sci. USA 86: 4823–4827; Grosshans, C. A. and Cech, T. R., 1991, Nucleic Acids Res. 19: 3875–3880; Taira, K. et al., 1991, Nucleic Acid Res. 19: 5125–5130). In addition, these structural units can be arranged in tandem to cleave multiple sites within a target gene, thus achieving greater effects (Yuyama, N. et al., 1992, Biochem. Biophys. Res. Commun. 186: 1271–1279). By using these kinds of ribozymes, the transcription products of the target genes of the present invention can be specifically cleaved, and the gene expression can be suppressed.

Suppression of endogenous gene expression may also be achieved by co-suppression resulting from transformation with a DNA comprising a sequence identical or similar to a target gene sequence. The term "co-suppression" refers to the phenomenon of suppression of expression of both the introduced exogenous gene and the target endogenous gene when a gene comprising a sequence identical or similar to that of the target endogenous gene is introduced into plants by transformation. The detailed mechanism of co-suppression is unknown, but it is frequently observed in plants (Smyth, D. R., Curr. Biol., 1997, 7: R793–5; Martienssen, R., 1996, Curr. Biol. 6: 810–813). For example, to obtain a plant in which an OsTUB8 gene is co-suppressed, plants of interest are transformed with a vector DNA constructed to express the OsTUB8 gene, or a DNA comprising a similar sequence, and plants with suppressed flowering compared to wild type plants are selected from the plants thus obtained. Genes to be used for co-suppression do not have to be completely identical to the target gene, however should comprise sequence identity of at least 70% or more, preferably 80% or more, more preferably 90% or more (for example, 95%, 96%, 97%, 98%, 99%, or more). Sequence identity may be determined using an above-described method.

In addition, suppression of endogenous gene expression in the present invention can also be achieved by transforming a plant with a gene comprising characteristics that are dominant-negative to the target gene. A gene comprising dominant-negative characteristics is a gene that, when expressed, comprises the function of eliminating or reducing the activity of an original endogenous gene of the plant.

Vectors that can be used in plant cell transformation are not particularly limited as long as they can express the inserted gene in plant cells. For example, vectors that comprise promoters for expressing genes in specific plant tissues (for example, the promoters of the present invention as mentioned below) and promoters for constitutively expressing genes in plant cells (for example, cauliflower mosaic virus 35S promoter) can be used. In addition, vectors comprising a promoter which is activated upon induction by an external stimulus can also be used. Herein, "plant cells" comprise various forms of plant cells, for example, suspension culture cells, protoplasts, plant sections, and calli.

A vector can be introduced to a plant cell using various methods known to those skilled in the art, such as polyethylene glycol methods, electroporation methods, Agrobacterium-mediated methods, and methods using a particle gun. Regeneration of plants from transformed plant cells is also possible using methods known to those skilled in the art, according to the type of plant cell (see, Toki, S. et al., 1992, Plant Physiol., 100: 1503–1507).

In rice, for example, many techniques for producing recombinant plants are already established, and are widely used in the field of the present invention. These methods include the method for introducing genes into protoplasts using polyethylene glycol and then regenerating plants (suitable for Indian strains of rice) (Datta, S. K., 1995, In Gene Transfer To Plants, Potrykus, I. and Spangenberg, G. Eds., pp. 66–74), the method for introducing genes into protoplasts using electric pulse and then regenerating plants (suitable for Japanese strains of rice) (Toki, S. et al., 1992, Plant Physiol., 100: 1503–1507), the method for directly introducing genes into cells using particle gun method and then regenerating plants (Christou, P. et al., 1991, Bio/technology, 9: 957–962), and the method for introducing genes via an Agrobacterium, and then regenerating plants (Hiei, Y. et al., 1994, Plant J., 6: 271–282). These methods can be appropriately used in the present invention.

Once transformant plants, into which the genome of a DNA of the present invention has been inserted, are obtained, it is possible to obtain offspring from these plants by sexual or asexual reproduction. From these plants, their offspring, or their clones, reproductive materials can be obtained (seeds, fruits, cuttings, tubers, tuberous roots, lines, calli, protoplasts, etc). Using these materials, these plants can be mass-produced. The present invention comprises plant cells introduced with a DNA of the present invention, plants comprising those cells, the offspring or clones of those plants, and the reproductive materials of those plants, their offspring, and their clones.

The fertility of plants produced in this way can be expected to differ from that of wild type plants. For example, plants in which the expression of DNA encoding OsTUB8 protein has been suppressed, by the introduction of antisense DNA or the like, are thought to be invested with male sterility. In rice, which is a valuable crop, the methods of the present invention can be used to regulate fertility so as to suppress self-pollination and force cross-pollination, thereby granting the valuable characteristic of hybrid vigor.

Furthermore, the present invention presents DNA comprising anther-specific promoter activity. An example of this kind of DNA is a genomic DNA upstream of a DNA encoding an OsTUB8 protein, for example, a DNA comprising the nucleotide sequence of SEQ ID NO: 3.

The promoter DNAs of the present invention include DNAs highly homologous to DNAs comprising the nucleotide sequence of SEQ ID NO: 3, so long as they comprise anther-specific promoter activity. An example of these kinds of DNA is a DNA with anther-specific promotor activity, comprising the nucleotide sequence of SEQ ID NO: 3, where one or more nucleotides are substituted, deleted, added, or inserted. Methods well known to those skilled in the art can be used to prepare this kind of DNA. For example, the site-directed mutagenesis method, which is well-known in the art, can be used for introducing mutations to DNA comprising the nucleotide sequence of SEQ ID NO: 3 (Kramer, W. and Fritz, H. J., 1987, Methods Enzymol., 154: 350–367).

In addition, DNAs highly homologous to DNAs comprising the nucleotide sequence of SEQ ID NO: 3 can also be obtained using general hybridization techniques (Southern, E. M., 1975, J Mol Biol, 98: 503–517) or PCR techniques (Saiki R. K. et al., 1985, Science, 230: 1350–1354; Saiki R. K. et al., 1988, Science, 239: 487–491). For example, by using a DNA comprising the nucleotide sequence of SEQ ID NO: 3 or a part thereof as a probe, and using an oligonucleotide that specifically hybridizes to a DNA comprising the nucleotide sequence of SEQ ID NO: 3 as a primer, DNAs highly homologous to a DNA comprising the nucleotide sequence of SEQ ID NO: 3 can be isolated from rice and other plants.

Alternatively, if DNAs highly homologous to DNA encoding the OsTUB8 protein of SEQ ID NO: 1 are obtained, the anther-specific expression of the acquired DNA is confirmed, then a genomic DNA upstream of this obtained genomic DNA is thought to comprise anther-specific promoter activity. DNAs encoding the OsTUB8 protein can be used in this way to obtain DNAs of the present invention comprising anther-specific activity.

The DNA promoters of the present invention are preferably derived from monocotyledons, more preferably derived from Gramineae, and most preferably derived from rice. However, so long as they comprise anther-specific promoter function, their derivation is not particularly limited.

Known reporter assays using reporter genes or such can be used to investigate whether or not DNAs prepared as described above comprise promoter activity. The reporter gene is not particularly limited, so long as its expression can be detected. For example, reporter genes generally used by those skilled in the art include the CAT gene, lacZ gene, luciferase gene, β-glucuronidase gene (referred to as GUS), and GFP gene, etc.

The expression level of the reporter gene can be determined using methods known to those skilled in the art, according to the type of reporter gene. For example, when using the CAT gene as the reporter gene, CAT gene expression level can be determined by measuring the acetylation of chloramphenicol, caused by the CAT gene product. When the lacZ gene is used as the reporter gene, its expression level can be determined by analyzing the colouring of a pigment compound due to the catalytic action of the gene expression product. The expression level of the luciferase gene as a reporter can be determined by measuring the fluorescence of a fluorescent compound, caused by the catalytic action of the luciferase gene expression product. The expression level of the GUS gene can be determined by analyzing the coloring of 5-bromo-4-chloro-3-indolyl-β-glucuronide (X-Gluc) or the luminescence of Glucuron (ICN), caused by the catalytic action of the GUS gene expression product. The expression level of the GFP gene can be determined by measuring fluorescence due to the GFP protein.

A promoter DNA of the present invention can be used for expressing an arbitrary gene in an anther-specific manner. "An arbitrary gene" means a DNA whose transcription can be induced by a DNA promoter of the present invention. Therefore, in addition to DNAs encoding proteins, examples of arbitrary genes include DNAs that encode RNAs (for example, DNAs encoding antisense RNAs, and DNAs comprising ribozyme activity).

The promoter DNAs of the present invention can be used to express an arbitrary gene in an anther-specific manner by: for example, 1) constructing a vector comprising a promoter DNA of the present invention; 2) operably linking the arbitrary gene downstream of the promoter DNA of the present invention in that vector; 3) introducing the DNA construct thus obtained to plant cells; and 4) regenerating these plant cells into a plant. "Operably linking" means binding an arbitrary gene to a promoter DNA of the present invention such that it can be expressed in response to the activation of the promoter DNA of the present invention. Since the promoter DNAs of the present invention comprise high anther-specific activity, it is preferable that the arbitrary genes are genes that can be particularly expressed in the anther. For example, the above-mentioned genes that relates to fertility of plants can be suitably used. General genetic engineering techniques can be used to construct a vector comprising a promoter DNA of the present invention. There is no particular limitation as to the plant cells to which the vector is introduced, however they are preferably derived from monocotyledons, more preferably derived from Gramineae, and most preferably derived from rice. The above-mentioned methods, known to those skilled in the art, can be used to introduce vectors to plant cells, to regenerate the plant cells to plants, etc.

The expression of OsTUB8 genes identified by the present inventors is significantly strong in the anther as compared with that in other tissues. Thus, it is thought that they will be useful as anther-specific markers in plant development and differentiation processes. By suppressing OsTUB8 gene expression in plants, it is possible to grant plants the characteristic of male sterility. On the other hand, by introducing an OsTUB8 gene to male sterile plants, fertility can be granted to them. Accordingly, OsTUB8 genes are thought to be valuable for use in cultivating plant varieties. In addition, since OsTUB8 gene promoters are thought to comprise anther-specific activity, they are useful to express arbitrary genes in an anther-specific manner.

Hereinbelow, the present invention will be specifically described using Examples, but it is not to be construed as being limited thereto.

EXAMPLES

Rice (variety: Nipponbare) was grown under conditions of 600 µmol/m²s white fluorescent light at 25° C., 75% humidity, and under a twelve-hour day/night cycle. Commercially available high-grade gibberellin ($GA_3$), brassinolide (BL), auxin (IAA), cytokinin (BA), and abscisic acid (ABA) were used. RNA for RNA blotting analysis was extracted using Chomczynski and Sacchi's method (Chomczynski, P. and Sacchi, N., 1987, Anal. Biochem., 162: 156–159). An oligotex-dT-30 mRNA purification kit (Takara) was used to prepare mRNA for microarray analysis.

Example 1

Exhaustive Analysis of Genes and Proteins that Respond to Gibberellin

Microarray analysis was carried out to screen for genes that correspond to gibberellin. A cDNA microarray comprising 8987 EST clones was used. mRNAs were prepared by treating the leaf sheaths of rice seedling with 10 µM $GA_3$ for 24 hours. Using 1 µg of these mRNAs, a reverse transcription reaction was carried out in the presence of 50 µM Cy5 dCTP (Amersham Pharmacia Biotech). After reacting for two hours at 42° C., the reaction was stopped. After heat-treating for three minutes at 94° C., the RNA was degraded by 15 minutes of NaOH treatment at 37° C., and cDNAs were recovered. Fluorescence-tagged cDNA probes were purified using a QIA QUICK PCR purification kit (QIAGEN). The methods of Yazaki, J. et al. were used for probe hybridization and microarray slide scanning (Yazaki, J., et al., 2000, DNA Research 7: 367–370). Data was analyzed by ARRAY VISION (Imaging Research).

Proteome analysis was further carried out to screen for proteins that respond to gibberellin. Proteins were extracted from an extract prepared by treating the leaf sheaths of rice seedling with 10 µM $GA_3$ for 24 hours. These proteins were isolated by two-dimensional electrophoresis using isoelectric focusing for the first dimension and SDS-PAGE for the second dimension (O'Farrell, P. H., 1975, J. Biol. Chem. 250: 4007–4021). After electrophoresis, proteins were stained with Coomassie brilliant blue. Proteins whose amounts are altered were detected by superimposing two electrophoretic images, and by analyzing them using an image analysis apparatus (Amersham Pharmacia Biotech). The β-tubulins were identified as a result of screening genes and proteins.

Figure 1A:
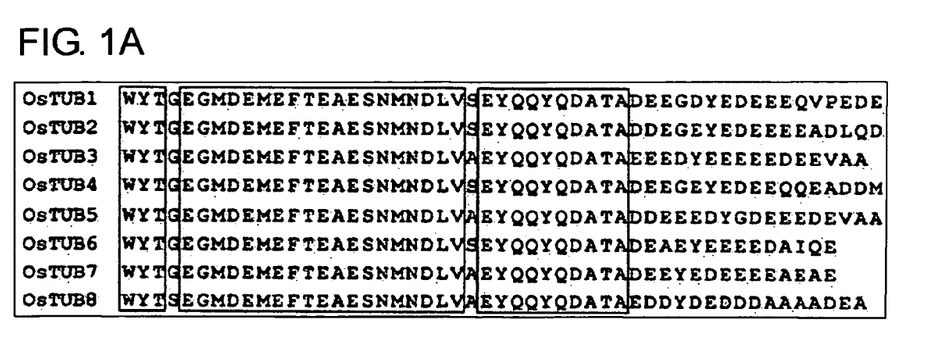
FIG. 1 shows a comparison of the C-terminal amino acid sequences of eight types of β-tubulins (from the top: SEQ ID NOs: 4 to 11), and a photograph comparing their specificities, according to Southern blotting. The eight types of β-tubulins comprise specific amino acid sequences in their C-terminals, and specific probes were thus constructed using these sequences.
Figure 1B:
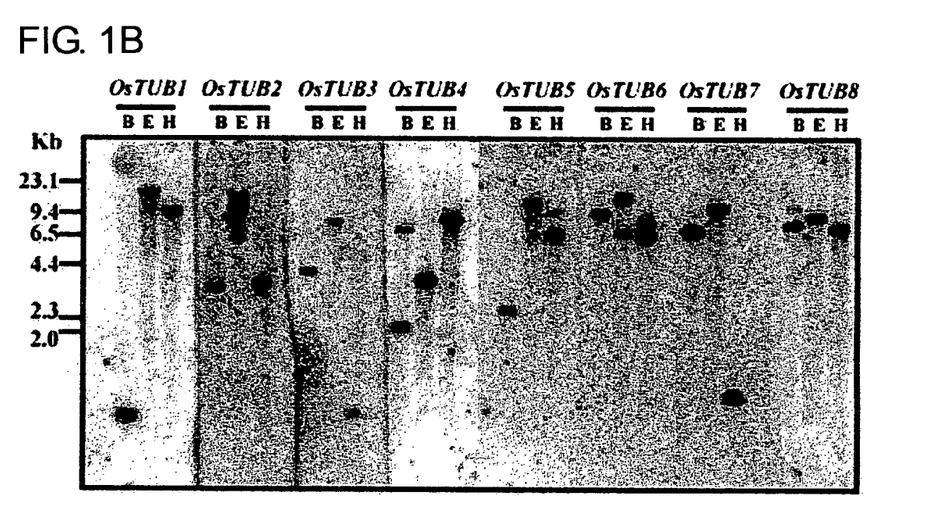

Primers were constructed specifically for eight types of β-tubulin, respectively. PCR was carried out using each β-tubulin EST clone as a template, and using a T3 primer and a primer specific to the 3'-untranslated region of each β-tubulin. After the reaction, the PCR products were purified from the gels. Their specificity was confirmed using Southern blotting (FIG. 1). The obtained PCR products were used as each tubulin-specific probe for Northern blotting analysis (see below).

Example 2

Analysis of Hormone Specificity in Rice Leaf Sheaths

About 0.5 g of tissue samples rapid frozen in liquid nitrogen was ground to a powder using a mortar and a pastle, and total RNA was prepared by the methods of Chomczynski and Sacchi (Chomczynski, P. and Sacchi, N., 1987, Anal. Biochem., 162: 156–159). For Northern blotting, 20 µg of total RNA was electrophoresed on a 1.2% agarose gel comprising 6% formaldehyde, and then transferred to a Hybond™-N⁺ nylon membrane (Amersham Pharmacia Biotech). The amounts of rRNA stained with ethidium bromide were compared with each other to ensure that equal amounts of RNA was electrophoresed in Northern blotting. Hybridization was carried out at 42° C. overnight using ULTRAhyb™ (Ambion), followed by washing with 2×SSC and 0.1% SDS at 42° C. for five minutes, and then with 0.1×SSC and 0.1% SDS at 68° C. for 15 minutes. The expression amount was analyzed using image analysis apparatus (Amersham Pharmacia Biotech).

Figure 2:
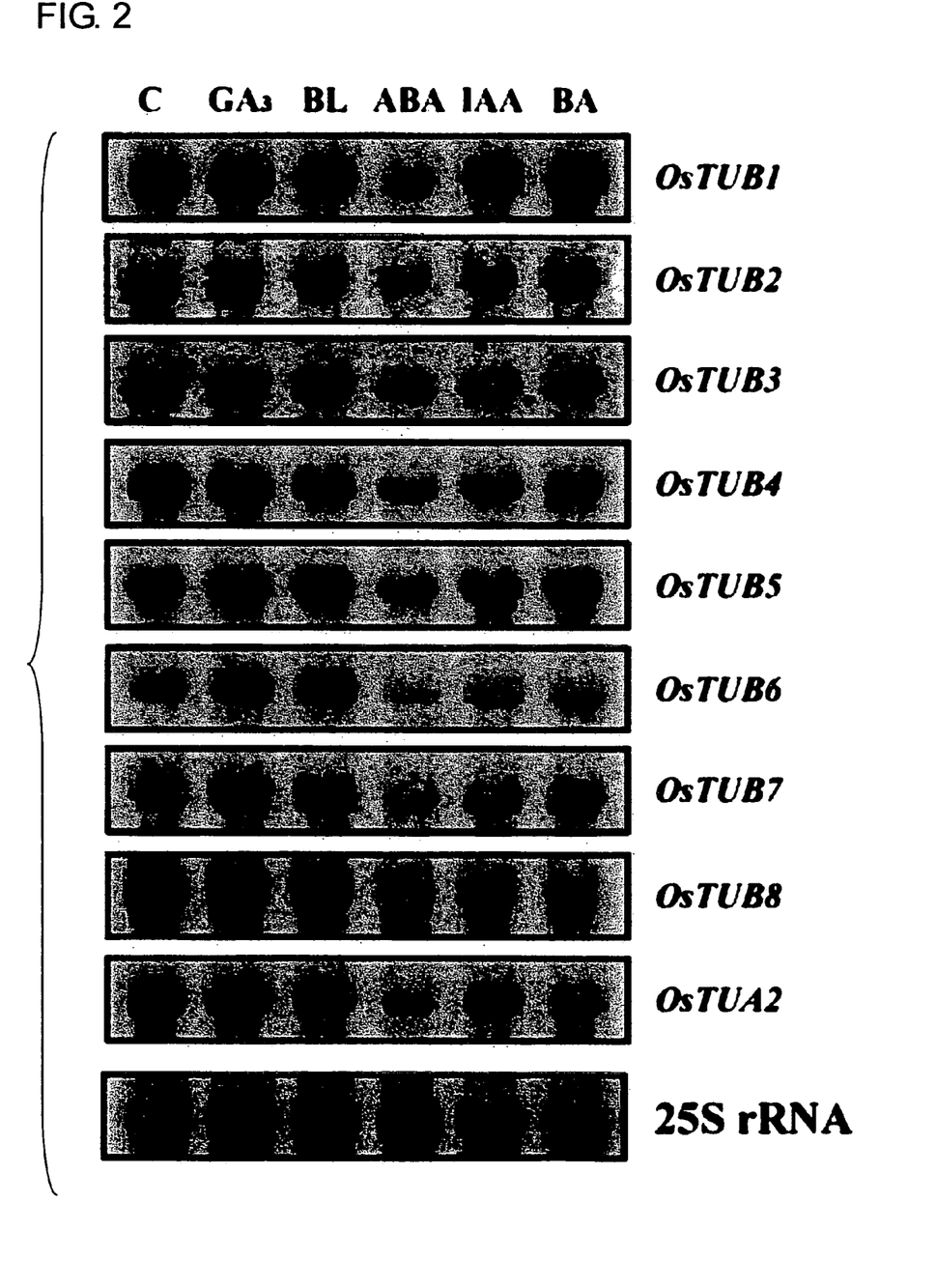

These results indicated that abscisic acid treatment suppressed the expression of all eight types of tubulin. The expressions of OsTUB5, OsTUB6, and OsTUB7 were increased by treatment with gibberellin and brassinolide, and in particular it was clear that treatment with gibberellin markedly increased the expression level (FIG. 2).

Example 3

Analysis of the Tissue-specificity of Tubulin

Figure 3:
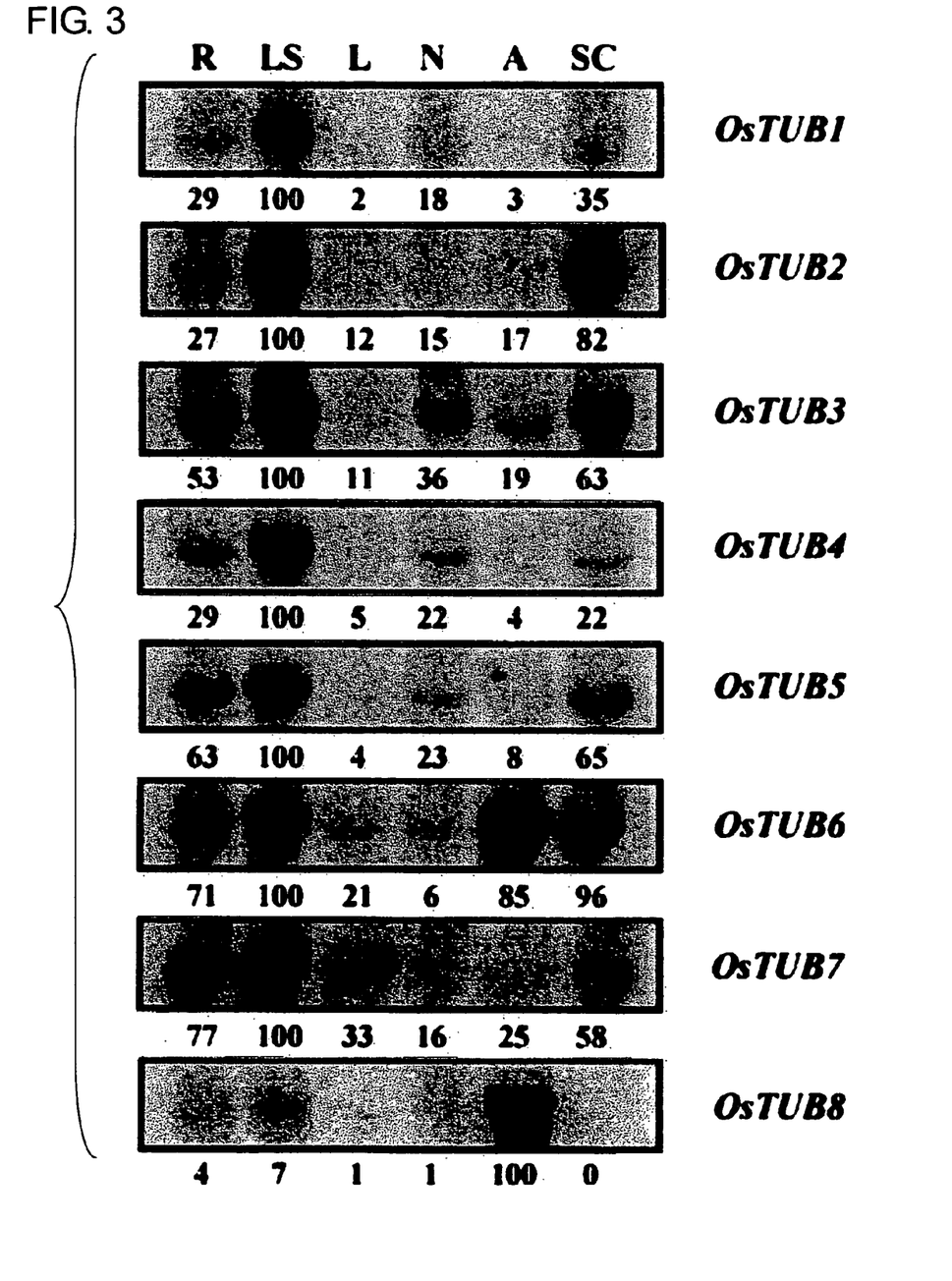

Using the above probes, Northern blotting was carried out to confirm the expression level of mRNAs in each rice tissue (FIG. 3), for analysis of the tissue-specificity of the eight types of tubulins. There was hardly any expression in the leaf blades for each of the eight types. OsTUB1, OsTUB3, OsTUB4, OsTUB5, and OsTUB7 were specifically expressed in rice leaf sheaths. OsTUB2 was expressed in leaf sheaths and calli, and OsTUB6 was expressed in leaf sheaths, calli, and anthers. OsTUB8 expression in the anther was 15 times more prominent than in leaf sheaths.

Example 4

Cloning of the Full-length cDNA

The full-length cDNAs were cloned by screening rice cDNA library, as well as by 5' RACE method using a SMART™ PCR cDNA synthesis kit (ClonTech). The cDNA nucleotide sequence was determined using a sequencer (Applied Biosystems).

Figure 4:
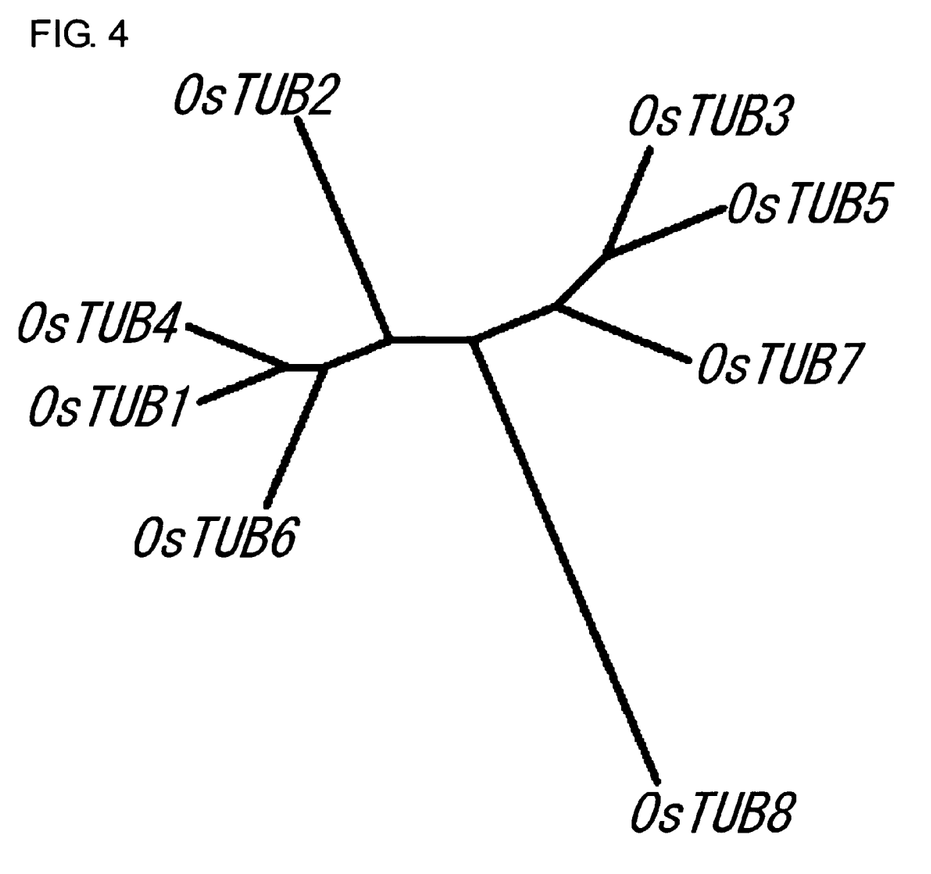
FIG. 4 is a figure showing a β-tubulin phylogenetic tree. The phylogenetic tree was analyzed using ClustalW software.

The obtained full-length OsTUB8 cDNA, which is about 90% homologous with other tubulins, consisted of 1,572 nucleotides and encoded 446 amino acids. OsTUB8 is a novel β-tubulin gene, unlisted in DDBJ and the like (SEQ ID NOs: 1 and 2). On constructing a β-tubulin phylogenetic tree, OsTUB8 was shown to be located away from the other β-tubulins (FIG. 4).

Example 5

Identification of OsTUB8 Promoter Regions

Homology searches revealed that OsTUB8 exists on rice genome BAC clone (AC139174), possessed by the International Rice Genome Sequencing Project. A 2 kbp region that presumably comprises a promoter region was confirmed to exist upstream of OsTUB8. The nucleotide sequence of the OsTUB8 promoter region as described above is presented in SEQ ID NO: 3.

What is claimed is:

1. An isolated DNA molecule that comprises anther-specific promoter activity and consists essentially of the nucleotide sequence of SEQ ID NO:3.

2. A vector comprising the DNA of claim 1.

3. The vector of claim 2 further comprising a heterologous nucleotide sequence of interest that is operably linked to the DNA of claim 1.

4. A transformed plant cell comprising the vector of claim 3.

5. A transformed plant comprising the transformed plant cell of claim 4.

6. A transformed plant clone or offspring of the transformed plant of claim 5 wherein said clone or offspring comprises the vector.

7. A reproductive material from the transformed plant of claim 5 wherein said reproductive material comprises the vector.

8. A reproductive material from the transformed plant clone or offspring of claim 6 wherein said reproductive material comprises the vector.

* * * * *